United States Patent [19]

Helioff et al.

[11] Patent Number: 4,834,767
[45] Date of Patent: May 30, 1989

[54] COMPOSITIONS USED IN PERMANENT ALTERATION OF HAIR COLOR

[75] Inventors: Michael W. Helioff, Westfield; Carmen D. Bires, Long Valley; Robert B. Login, Oakland, all of N.J.

[73] Assignee: GAF Corporation, Wayne, N.J.

[21] Appl. No.: 60,284

[22] Filed: Jun. 10, 1987

[51] Int. Cl.$^4$ .................. A61K 7/13; A61K 7/135
[52] U.S. Cl. ................................. 8/416; 424/62; 8/406
[58] Field of Search ............ 540/451, 531; 546/243; 548/550; 424/70, 71, 72, DIG. 3, DIG. 4, 62, 63, 64, 69; 8/416

[56] References Cited

U.S. PATENT DOCUMENTS

| | | | |
|---|---|---|---|
| 3,910,862 | 10/1975 | Barabas et al. | 424/71 X |
| 3,929,735 | 12/1975 | Barabas | 424/70 X |
| 4,283,384 | 8/1981 | Jacquet et al. | 424/70 X |
| 4,457,912 | 7/1984 | Scodari | 424/71 X |
| 4,590,069 | 5/1986 | Deckner et al. | 424/69 X |
| 4,612,188 | 9/1986 | Zorayan et al. | 424/70 X |
| 4,732,990 | 3/1988 | Login et al. | 546/243 X |

FOREIGN PATENT DOCUMENTS 873891 7/1949 Fed. Rep. of Germany ........ 424/71

Primary Examiner—Joseph Paul Brust
Attorney, Agent, or Firm—Marilyn J. Maue; Joshua J. Ward

[57] ABSTRACT

A permanent hair color altering composition comprising an aqueous preparation on the basis of melanin dissolution and/or oxidation of a hair colorant dye intermediate, which contains as a swelling and penetration agent, a quaternized amino lactam having the formula:

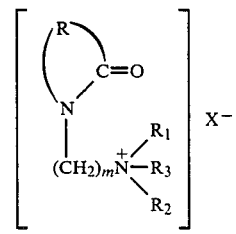

wherein m is an integer having a value of from 1 to 4; R is alkylene having from 3 to 8 carbon atoms and is optionally substituted with $C_1$ to $C_4$ alkyl; $R_1$, $R_2$ and $R_3$ are each independently selected from the group of alkyl, alkyleneoxy alkyl, alkylhydroxy, alkoxy, aryl, aralkyl, alkaryl, and alkylene amidoalkyl radicals, said groups each having from 1 to 30 carbon atoms and at least one of $R_1$, $R_2$ and $R_3$ is a radical having from 8 to 30 carbon atoms; and $X^-$ is a chloride, bromide or iodide anion. The invention also relates to the use of said quaternized compounds.

28 Claims, No Drawings

COMPOSITIONS USED IN PERMANENT ALTERATION OF HAIR COLOR

This application is a continuation-in-part of co-pending U.S. patent application Ser. No. 922,923, filed Oct. 24, 1986, entitled "QUATERNIZED NITROGEN CONTAINING COMPOUNDS" now U.S. Pat. No. 4,732,990.

In one aspect the invention relates to an aqueous composition containing a stable conditioning, softening and penetrating agent for hair undergoing treatment with a color altering formulation.

In another aspect the invention relates to an agent which enhances the dissolution of melanin and promotes penetration of an oxidation dye intermediate into a hair follicle.

In still another aspect the invention relates to an additive for a hair bleaching composition and, in yet another aspect an additive for a permanent hair coloring shampoo composition.

BACKGROUND OF THE INVENTION

The main coloring component of hair is a dark pigment, melanin, which occurs as granules embedded in the hair cortex. The aim of bleaching is to decolorize selectively the natural pigments or applied pigments in the hair with minimal damage to the hair matrix. When hair is bleached, the color changes to lighter and lighter shades depending upon the amount of melanin granules dissolved and removed from the hair fiber. Hydrogen peroxide is the leading solvent for melanin used in the bleaching process; however, along with melanin removal, the peroxide reacts with keratin to cause loss of tensile properties and damage to the hair. More specifically, bleaching occurs in two steps: (1) initial solubilization of the color granules and (2) decolorization of the dark brown solubilized pigment. The reaction between melano-protein and hydrogen peroxide is confined mainly to the protein-combined cystene residues which are subsequently converted to combined cysteic acid. The solubilization of the melanin granules is connected with the splitting of the disulfide bridges in the melano protein and it is likely that the disulfide bridge may be the stabilizing factor in melanin, as it is in keratins.

The bleaching process can be halted at any point or can be permitted to continue to a light blonde or platinum shade. The latter provides a good background for a variety of tints which can be obtained by a subsequent coloring step. Such bleaching and coloring combination is known as a double process coloring and causes hair damage by promoting porosity, brittleness, loss of tensile strength and dryness.

Permanent hair colorants involve the use of oxidation dye intermediates which are colorless substances but which, when mixed with oxidizing agents just prior to use, produce color by a process of oxidative condensation. More specifically, the intermediates, in the presence of an oxidant, couple with another oxidation dye intermediate molecule to form a large fused ring color compound within the hair fiber. Since the fused ring product is too large to penetrate the hair fiber, it is essential that good penetration is achieved by the precursor intermediate. The oxidation dye process engenders many changes in the chemical and cosmetic characteristics of the hair which are undesirable. Specifically, the effect of alkali swelling of the hair fiber leads to loss of tensile strength, flexibility and promotes a porous, dry appearance. Additionally, the oxidation dye intermediates often cause skin sensitivity and reddening. Still further, the color imparted on processed hair is often non-uniform since the preprocessed sections, have higher porosity and absorb the interemediate at a faster rate than virgin growth which is more resistant to absorption.

Certain quaternized amine compounds and polymeric amines as disclosed in U.S. Pat. No. 4,532,127 and U.S. Pat. No. 4,579,732 have been developed to overcome some of the above problems. However these basic compounds have not been found to be completely satisfactory since they react with anionic components which are commonly present in hair coloring or bleaching compositions. This reactivity causes undesirable alterations in the shade desired. Additionally the amino groups react with hydrogen peroxide to form nitrogen oxides, thus increasing the effective amount of peroxide which must be employed in bleaching compositions. Since peroxides are known to have a drying effect on hair, it is desirable to use as little as possible to obtain the desired effect. Further the relatively high viscosity of the polymeric compounds together with the normal variation in molecular weight of the polymer chains in the product lead to formulation problems in reproducability of product quality and in storage of the product over extended periods. In addition the large molecular size of the polymeric products prevents their penetration into the hair fiber and instead forms a coating over the hair, which may develop tack under conditions of high humidity. Finally, many hair dye and bleaching compositions produce a disagreeable odor which the prior quaternized amino compounds do not mask.

Accordingly, it is an object of this invention to overcome or minimize the above deficiencies by providing a chemically stable additive which obviates skin sensitization, conditions the hair during processing, aids in the penetration of dye intermediate without undue alkaline swelling of the hair fiber, provides complexing sites on which the colorant can form, minimizes the period of hair exposure to chemical solutions, provides a more uniform distribution of color to processed hair by promoting penetration in portions of new hair growth, preserves the tensile properties of bleached or dyed hair and successfully masks undesirable thiol odors.

These and other objects of the invention will become apparent from the following description and disclosure.

THE INVENTION

In accordance with the present invention there is provided a quaternized amino lactam which is incorporated into a permanent hair color altering formulation at a concentration of between about 0.01 to about 12 wt. %, preferably between about 0.5 and about 7.5 wt. % based on total weight of the treating formulation. The lactams of the present invention are defined by the structure

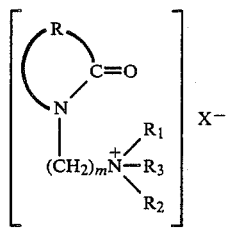

wherein m is an integer having a value of from 1 to 4; R is alkylene having from 3 to 8 carbon atoms and is optionally substituted with $C_1$ to $C_4$ alkyl; $R_1$, $R_2$ and $R_3$ are each independently selected from the group of alkyl, alkyleneoxy alkyl, alkylhydroxy, alkoxy, aryl, aralkyl, alkaryl, and alkylene amidoalkyl radicals, said groups each having from 1 to 30 carbon atoms and at least one of $R_1$, $R_2$ and $R_3$ is a radical having from 8 to 30 carbon atoms; and $X^-$ is a chloride, bromide or iodide anion, preferably a chloride anion. Of these, lactams having the formula

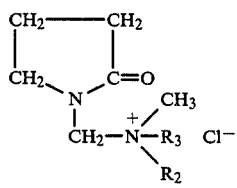

are preferred and include those pyrrolidones wherein at least one of $R_2$ and $R_3$ is octadecyl, hexadecyl, tetradecyl, hydrogenated tallow or coco and wherein the other of $R_2$ and $R_3$ is methyl or the same as $R_3$. Most preferred are the pyrrolidones wherein $R_3$ is hexadecyl or octadecyl which are employed in a concentration of between about 0.75 and about 5.0 wt. %. The present hair bleaching or oxidation dye intermediate formulations or compositions containing an oxidation dye intermediate including a permanent shampoo tint, a permanent hair dye, hair bleach, hair blanch or hair dye removal preparation for home or professional use. Alternatively, such color altering preparations may be made up using the components normally included in preparations currently marketed and the lactams of this invention added to improve properties and minimize hair damage.

Generally, the permanent hair dye formulations of this invention are those employed for changing the color of hair, covering up white hair, shading the hair after lightening or simultaneous bleaching and dyeing or double process blonding to provide color alteration of long color durability.

The permanent dye formulations of this invention conventionally include an oxidation dye intermediate such as an analog or a derivative of a phenylene diamine, an aminophenol, a phenol or naphthol which, upon oxidation couples with itself or another analog or derivative of phenylene diamine to form a large fused ring compound having at least one unsaturated chromophoric bond within the hair fiber. The color developed from the colorless intermediate depends on the substituents or terminal groups of the diamine, for example, such groups as an aromatic amine or phenol, an aromatic nitro group or trace amounts of heavy metal. Other factors which alter the shade of the dyed hair include concentration, alkaninity, base composition and the combination of intermediates involved in the oxidation reaction. The dyeing or bleachiing of hair generally requires from about 10 to about 40 minutes of processing time. Use of the present lactams can reduce processing time by at least 10%. The following Table I provides a representative group of dye intermediates, color couplers and modifiers employed to obtain specific hair shades. Also, any of the dyes disclosed in U.S. Pat. No. 4,532,127 are suitably employed in this invention.

TABLE I

| Black | Dark/medium brown | Light brown | Reddish | Blonds | Blue/gray; modifiers |
|---|---|---|---|---|---|
| p-aminodiphenyl-amine | p-aminodiphenyl-amine | o-aminophenol | 2-amino-4-nitrophenol | p-aminodiphenylamine-sulfonic acid | p-aminodiphenylamine hydrochloride |
| p,p'-diaminodi-phenylamine | o-aminophenol | p-aminophenol-hydrochloride | 4-amino-2-nitrophenol | 4-amino-2-nitrophenol | N—(p-aminophenyl)-glycine |
| 2,5-diaminophenol-4-sulfonic acid | p-aminophenol | p,p'-diamino-diphenylamine | 2,4-diaminophenol | p-aminophenol hydro-chloride | 2,4-diaminoanisole |
| 1,8-diaminonaph-thalene | N—(p-aminophenyl)-glycine | 2,4-diaminophenol | 4,6-dinitro-2-amino-phenol | 2-aminophenol-4-sul-fonic acid | p,p'-diaminodiphenyl-methane |
| o-phenylenediamine | o-anisidine | 2-nitro-p-phenylenediamine | 5-nitro-m-phenylene-diamine | 4-aminophenol-2-sul-fonic acid | 2,4-diaminophenetole |
| p-phenylenediamine | 2,4-diaminophenol | m-phenylene-diamine | 4-nitro-o-phenylene-diamine | 5-aminophenol-2-sul-fonic acid | 1,5-naphthalenediol |
| m-toluenediamine | N,N—dimethyl-p-phenylenediamine | p-phenylene-diamine hydrochloride | 2-nitro-p-phenylene-diamine | 2,5-diaminophenol-4-sulfonic acid | m-phenylenediamine |
| p-toluenediamine | N—(p-hydroxy-phenyl)-glycine | p-tolylenediamine | 2,4,6-trinitroaniline | N—(2-hydroxy-5-nitro-phenyl)glycine | pyrocatechol |
|  | p-methylaminophenol |  |  | N—(p-nitrophenyl)glycine m-phenylenediamine hydrochloride | pyrogallol resorcinol |
|  | 4-nitro-o-phenylenediamine |  |  |  |  |
|  | m-phenylenediamine |  |  | p-phenylenediamine sulfate | p-tolylenediamine |
|  | p-phenylenediamine |  |  |  |  | lactams pyrrolidones are beneficially incorporated into the color altering formulation just before use.

As "formulation" is used herein, it is to be understood that this term includes a cream, a gel, an emulsion or a watery liquid or detergent solution.

The present lactams can be used individually or in admixtures and can be added to any of the commercial Other compounds which act as color modifiers or couplers include m-diamines, m-amino phenols, polyhydroxy phenols, which are also stabilizers and antioxidants, and naphthols. The later are often used as secondary dye intermediates in the formulation. Pyridine derivatives have also been suggested for use as a dye intermediate in place of phenylene diamines. In some cases direct dyes can be added to the formulations to provide color highlights.

The color vehicle for the dye intermediates is employed at a pH usually between about 9 and 11 which can be adjusted with ammonium hydroxide to the desired level of alkalinity. The ammonium hydroxide base is preferred since ammonia assists in swelling the hair fiber and by being easily removed. More specifically, the color vehicle is an aqueous solution of soap or synthetic detergent which provides wetting and penetration of the dye intermediate. Ammonium oleate, alkanol amides and shampoo detergents such as fatty alkyl sulfates, fatty acid polypeptide condensates and oxyethylated fatty alcohols are most commonly employed.

In addition to the dye intermediate and color vehicle, formulations may also include interemediate solubility aids such as propylene glycol, ethyl alcohol or isopropyl alcohol and conditioners such as glycerol, lanolin, oleyl alcohol, cetyl alcohol, etc. and antioxidants such as a sulfite, primarily sodium sulfite or bisulfite, and thioglycolic acid which are usually included to prevent premature oxidation. The addition of the present lactams to this formulation obviates the need for other conditioners, promotes penetration of the intermediate into the hair fiber particularly in the areas of new growth, substantially reduces skin sensitization, promotes hair fiber swelling and results in a more uniform distribution of color while giving the hair a soft, silky, conditioned texture after processing. Also, the lactam moiety, particularly the pyrrolidonyl moiety of the present compounds, exerts a stabilizing effect on the quaternized amino group so that the present compounds do not react with peroxides or anionic components. This stabilizing effect enables the use of smaller amounts of these components to achieve the desired effect.

Although the practical amount of lactam added to the formulation is within the range of from about 0.01 to about 7.5 wt. % of the total formulation, it is to be understood that larger amounts, up to about 12 wt. % can be employed without deleterious effect, economics being the limiting consideration.

The oxidation dye intermediate formulation is applied to the hair with a oxidation dye developer. The developer is an oxidant mixed with the intermediate formulation just before application and is usually applied in equal parts with the intermediate formulation; although when hydrogen peroxide is used as the developer, between about 1.5 and about 2 parts peroxide per part of intermediate can be used to cause bleaching and coloring in a single application. Creams or aqueous solutions of 5 to 7% hydrogen peroxide or urea peroxide are the primary developers commercially employed. However other developers which have been suggested include chloroates, persulfates, perborates and sodium dichromate. The lactams of this invention can also be added to the developer formulation for more uniform distribution and/or thickening effect as in cream applications.

The above dye components are often formulated into shampoos with oleate soaps or ethoxylated fatty alcohols to prevent drip and run-off.

The hair dye operations may be followed by a final conditioning treatment, a neutralizing rinse or an acid balanced shampoo containing in addition to cationic or amphoteric surfactants, cation-active emollients. The present lactams may also be added to such neutralizing applications for conditioning effect.

Some typical hair dye formulations are illustrated by the following

| OXIDATION DYE INTERMEDIATE | |
|---|---|
| Ingredients | % by Wt. |
| A. ASH BLONDE HAIR DYE | |
| Oleic acid | 35.00 |
| Ethoxylated Sorbitan | 10.00 |
| Oleate (5 Mole Ethoxylate) | 3.50 |
| Soriban Oleate | |
| PEG-40 Sorbitan Lanolate | 1.75 |
| Lecithin Hydroxylated | 1.25 |
| EDTA (ethylene diamine tetra acetic acid) | 0.10 |
| Sodium Sulfite | 0.50 |
| Deionized/Distilled Water | 31.19 |
| Ammonium Hydroxide, 28% | 10.00 |
| Isopropyl Alcohol | 2.50 |
| P—Phenylenediamine | 0.60 |
| O—Aminophenol | 0.10 |
| P—Aminophenol | 0.01 |
| 4-Nitro-1,2-Diaminobenzene | 0.30 |
| Pyrogallol | 0.70 |
| Resorcinol | 0.20 |
| Hydroquinone | 0.10 |
| Perfume | 0.20 |
| N—n-Dodecyl Pyrrolidone | 2.00 |
| | 100.00 |
| B. BLUE VIOLET HAIR DYE | |
| Oleic acid | 35.00 |
| Ethoxylated Sorbitan | 10.00 |
| Oleate (5 Mole Ethoxylate) | 3.50 |
| Soriban Oleate | |
| PEG-40 Sorbitan Lanolate | 1.75 |
| Lecithin Hydroxylated | 1.25 |
| EDTA (ethylene diamine tetra acetic acid) | 0.10 |
| Sodium Sulfite | 0.50 |
| Deionized/Distilled Water | 29.90 |
| Ammonium Hydroxide, 28% | 10.00 |
| Isopropyl Alcohol | 2.50 |
| P—Phenylenediamine | 0.55 |
| P—Aminophenol | 0.90 |
| 1,5 Dihydroxy naphthalene | 0.80 |
| 2,4-Diaminoanisole Sulfate | 0.25 |
| Pyrocatachol | 0.80 |
| Perfume | 0.20 |
| N—n-Dodecyl Pyrrolidone | 2.00 |
| | 100.00 |
| C. BLACK HAIR DYE | |
| Oleic acid | 35.00 |
| Ethoxylated Sorbitan | 10.00 |
| Oleate (5 Mole Ethoxylate) | 3.50 |
| Soriban Oleate | |
| PEG-40 Sorbitan Lanolate | 1.75 |
| Lecithin Hydroxylated | 1.25 |
| EDTA (ethylene diamine tetra acetic acid) | 0.10 |
| Sodium Sulfite | 0.50 |
| Deionized/Distilled Water | 29.29 |
| Ammonium Hydroxide, 28% | 10.00 |
| Isopropyl Alcohol | 2.50 |
| P—Phenylenediamine | 3.75 |
| *2,4-Diaminoanisole,1; P—Phenylenediamine,2 | 0.05 |
| 1,5-Dihydroxy naphthalene | 0.06 |
| P—Aminodiphenylamine | 0.05 |
| Perfume | 0.20 |
| N—n-Dodecyl Pyrrolidone | 2.00 |
| | 100.00 |
| D. MEDIUM RED HAIR DYE | |
| Oleic acid | 35.00 |
| Ethoxylated Sorbitan | 10.00 |
| Oleate (5 Mole Ethoxylate) | 3.50 |
| Soriban Oleate | |
| PEG-40 Sorbitan Lanolate | 1.75 |
| Lecithin Hydroxylated | 1.25 |
| EDTA (ethylene diamine | 0.10 |

| OXIDATION DYE INTERMEDIATE | |
|---|---|
| Ingredients | % by Wt. |
| tetra acetic acid) | |
| Sodium Sulfite | 0.50 |
| Deionized/Distilled Water | 23.25 |
| Ammonium Hydroxide, 28% | 10.00 |
| Isopropyl Alcohol | 2.50 |
| 2-Nitro-p-Phenylenediamine | 2.50 |
| 4-Nitro-o-Phenylenediamine | 0.50 |
| P—Phenylenediamine | 1.00 |
| P—Aminophenol | 1.00 |
| *4-Nitro-o-Phenylenediamine,1; 2-Nitro-p-Phenylenediamine,1 | 0.15 |
| 4-Amino-2-Nitrophenol | 1.50 |
| Pyrogallol | 2.0 |
| Resorcinol | 1.3 |
| Perfume | 0.20 |
| N—n-Dodecyl Pyrrolidone | 2.00 |
| | 100.00 |

*fusion mixtures

The same developer solution can be used for each of the above hair dyes. The following formulation is representative of a suitable developer.

| Ingredient | % by Wt. |
|---|---|
| Hydrogen Peroxide, 30% | 20.00 |
| Nonoxynol-9 | 5.00 |
| Nonoxynol-4 | 2.00 |
| Phosphoric Acid | 0.50 |
| Cetyl Alcohol | 0.50 |
| Stearyl Alcohol | 0.50 |
| Deionized Water | 71.50 |
| | 100.00 |

If desired lactam can be added to the above developing formulation instead of to the dye formulation or the amount of lactam can be divided between both the dye and developer formulations. The concentration of lactam in-dye and developer system can range between about 0.75% and about 7.5% by weight, preferably between about 1% and about 5% by weight.

Bleaching involves a process for partial or complete oxidative degradation of the natural color pigment, i.e. melanin granules mainly present in cortex of hair fiber, or removal of applied dye pigment in or on the hair. As a side reaction, bleaching also attacks the hair cuticle proteins, i.e. the keratin protein, and causes oxidative modifications of both the cuticle and cortex proteins; thus decolorizing dissolved melanin or color granules and reducing the cross-linking capacity of cystine by oxidation to cysteic acid.

The most common bleaching agent comprises an aqueous solution of hydrogen peroxide of between about 5 to 9% strength in a formulation adjusted to a pH of from about 9 to about 11; although urea peroxide and other hydrogen peroxide creams incorporating a thickening agent such as a fatty alcohol or an alkanolamide can also be used.

The peroxide bleaching agent is employed with an activator which is added just before use, ammonium hydroxide being preferred by most practitioners since the ammonia swells the hair fiber to allow for peroxide penetration and is volatile which permits easy removal. Other activators which have been employed include sodium carbonate and ethanolamines. Bleach accelerators and boosters such as persulfate salts of ammonia, potassium and sodium may be used as well and conditioners e.g. ammonium oleate soap, a lipophilic surfactant, cholesterol and lanolin derivatives, are generally included in the peroxide formulation. Notwithstanding the generous use of such conditioning agents, noticeable drying, splitting and texture loss to the hair occurs. Subsequent reoxidation restores the cystine of most of the cysteine residues formed during reduction to disulfide bonds. Reported recoveries are approximately 90%. Still, the bleaching process causes damage such as tangles, dryness, brittleness, greater porosity, swelling, frizzing, etc.

The present lactams can be added to these formulations in the above amounts to minimize skin sensitivity, to preserve the tensile properties of the hair and to provide a strong conditioning action by forming a thin film over the hair cuticle which eliminates or minimizes hair dryness and breakage. Also, because of their high penetrating power and hair swelling properties, the present lactams are capable of diminishing the time hair is exposed to the chemical oxidation process.

Some typical hair bleaching formulations include the following.

| Ingredient | % by Weight |
|---|---|
| BLEACH FORMULATION A | |
| Polyethylene glycol oleyl ether | 14.02% |
| Oleic acid | 7.01 |
| Ethanol | 4.67 |
| Monoethanolamine | 2.80 |
| Ethoxylated nonyl phenol | 2.33 |
| $H_2O_2$ 50% | 6.89 |
| K persulfate | 2.95 |
| $NH_4$ persulfate | 0.92 |
| Na persulfate | 2.95 |
| Disodium EDTA | 0.13 |
| Na metasilicate | 6.15 |
| $H_2O$ | 49.18 |
| BLEACH FORMULATION B | |
| Cetyl Alcohol | 2.50 |
| Glyceryl Monostearate and Polyethylene Glycol 100 Stearate [Arlacel 165] | 2.50 |
| Deionized $H_2O$ | 86.43 |
| Hydrogen Peroxide, 35% (dilution grade) | 8.57 |
| Phosphoric Acid, 10% C.P. | to pH 3.5 to 4.0 |
| | 100.00 |
| BLEACH FORMULATION C (CREAM FORM) | |
| Cetyl Alcohol | 10.00 |
| Glyceryl Monostearate and Polyethylene Glycol 100 Stearate [Arlacel 165] | 2.50 |
| Deionized Water | 70.36 |
| Hydrogen Peroxide, 35%, (dilution grade) | 17.14 |
| Phosphoric Acid, 10% C.P. | to pH 3.5 to 4.0 |
| | 100.00 |

Other areas in the cosmetic color alteration of hair where the lactams of this invention can be applied include hair blanching which employs sulfur dioxide or potassium permanganate followed by sodium thiosulfate to convert hair of mixed grey to snowy white and processes for certain hair dye removal techniques which employ a weak solution of sodium hydrosulfite, sodium thiosulfate or aminoiminomethane sulfinic acid.

The present lactams, particularly the pyrrolidones, can be incorporated into any of the foregoing formulations simply by mixing in the prescribed amount, preferably just before use, at ambient temperature and pressure and mixed for a period sufficient to provide uniform distribution.

Having thus generally described the invention, reference is now had to the following examples which illustrate preferred embodiments but which are not to be construed as limiting to the scope of the invention as more broadly set forth above and in the appended claims.

EXAMPLE 1

An evaluation of the quaternized lactam, dimethyl octadecyl-[N-(2-pyrrolidonyl)methyl]ammonium chloride additive in a standard type of hair bleach (Helene Curtis White Frosting Bleach) was made as described below.

Each of the representative compositions X and Y comprising the hair bleach formulation were divided into equal portions. The first divided portions X-Y were combined and immediately applied to portions of the hair selected for frosting on the left side of the scalp of the subject undergoing testing. The subject had (color) hair of good texture and quality. To the remaining divided X-Y portions, after being combined, 1 wt. % of the quaternized dimethyl octadecyl-[N-(2-pyrrolidonyl)methyl]ammonium chloride was added. The later mixture of combined X-Y portions, containing the quaternized lactam, was applied to equal portions of the hair selected for frosting on the right side of the scalp of said subject.

|  | Wt. % |
|---|---|
| X. Ingredients in Bleach |  |
| Polyoxyethylene glycol oleyl ether | 14.02 |
| Citric acid | 7.01 |
| Ethyl alcohol | 4.67 |
| Monoethanol amine | 2.80 |
| Ethoxylated nonyl phenol | 2.33 |
| $H_2O_2$ (50%) | 6.89 |
| Potassium persulfate | 2.95 |
| Ammonium persulfate | 0.92 |
| Sodium persulfate | 2.95 |
| Disodium ethylenediamine tetra acetic acid | 0.13 |
| Sodium metasilicate | 6.15 |
| Deionized distilled water | 49.18 |
| Y. Developer |  |
| $H_2O_2$ (30%) | 20.00 |
| Nonoxynol-9 | 5.00 |
| Nonoxynol-4 | 2.00 |
| Phosphoric acid | 0.50 |
| Cetyl alcohol | 0.50 |
| Stearyl alcohol | 0.50 |
| Water | 71.50 |

The combined lotions on each side of the scalp were separately maintained on the hair for the prescribed period, 30 minutes, after which the lotions were rinsed away with water. The hair was blown dry and the following evaluations comparing the hair on the right and left side of the scalp were made. The results are reported in Table II.

TABLE II

|  | Left Side | Right Side |
|---|---|---|
| BLEACHING PROCESS |  |  |
| Ease of Application | good | excellent |
| Processing Time | 30 min. | 30 min. |
| Scalp and Skin Irritation | none | none |
| Ease of Rinse-Out | good | good |
| WET EVALUATION OF HAIR |  |  |
| Feel | fair | excellent |
| Dryness | slight dryness | completely conditioned |
| Combability | fair | excellent |
| Manageability | good | excellent |
| Snarling | some | none |
| Porosity | slight | none |
| DRY EVALUATION OF HAIR |  |  |

TABLE II-continued

|  | Left Side | Right Side |
|---|---|---|
| Combability | fair | excellent |
| Snarling | some | none |
| Degree of Bleach | yellow | very pale yellow |
| Breakage | none | none |
| Softness | good | better |
| Body | good | excellent |
| Manageability | good | excellent |
| Conditioning | smooth | smoother |
| Luster | good | excellent |
| HAIR CONDITION AFTER 3 WEEKS |  |  |
| Color | yellow | very pale yellow |
| Blending (on hair shaft) | fair | excellent |
| Coverage at ends | fair | excellent |
| Lifting of color (pigmented hair) | good | excellent |
| Color Retention | good | excellent |
| Fading | some | very little |
| Skin and Scalp Irritation | none | none |

EXAMPLE 2

The quaternized lactam, dimethyl octadecyl-[N-(2-pyrrolidonyl)methyl]ammonium chloride was also evaluated as an additive to a standard hair dye formulation namely (Loving Care-Medium Brown). Each of the representative compositions A, B and C comprising the hair dye formulation were divided in equal portions. The first divided portions A-C were combined and immediately applied to the left side of the hair on the scalp of the subject undergoing testing. The subject had dark brown and grey hair of fine texture and quality. To the remaining divided portions A-C, after being combined, 1 wt. % of the quaternized dimethyl octadecyl-[N-(2-pyrrolidonyl)methyl]ammonium chloride was added. The later combined A-C portion, containing the quaternized lactam, was applied to the hair on the right side of the scalp of said subject.

|  | Wt. % |
|---|---|
| A. Ingredients for Color |  |
| Water | qs |
| Tall oil acid | 7.50 |
| Propylene glycol | 4.40 |
| Iso $C_3$ alcohol | 4.35 |
| Octoxynol-1 | 3.50 |
| Nonoxynol-4 | 2.00 |
| $NH_4OH$, 26° Baume | 1.15 |
| Ethoxydiglycol | 0.75 |
| Cocamide diethanolamide | 3.50 |
| Polyethyleneglycol-8 tallow amine | 0.50 |
| Sulfated Castor Oil | 1.50 |
| Erythorbic Acid | 0.50 |
| Ethylenediaminetetraacetic acid | 0.01 |
| Glycol | 0.25 |
| Na sulfite | 0.05 |
| N,N—bis(2-hydroxyethyl)-p-phenylenediamine sulfate | 0.18 |
| 1-Naphthol | 0.08 |
| Resorcinol | 0.31 |
| p-Phenylenediamine | 0.35 |
| Fragrance | 0.50 |
| Adjust pH to 9.8 |  |
| B. Ingredients for Developer |  |
| $H_2O_2$, 30% | 20.00 |
| Nonoxynol-9 | 5.00 |
| Nonoxynol-4 | 2.00 |
| Phosphoric Acid | 0.50 |
| Cetyl Alcohol | 0.50 |
| Stearyl Alcohol | 0.50 |
| Water | 71.50 |
| C. Ingredients in Conditioner Lotion |  |
| Hydroxyethyl Cellulose | 1.00 |
| Ethoxydiglycol | 0.50 |

-continued

| | Wt. % |
|---|---|
| Polyquaternium - 6 | 0.50 |
| Cocoamphocarboxypropionate | 25.00 |
| Cocamidopropyl Betaine | 10.00 |
| Glycol | 5.00 |
| Quaternium - 15 | 0.25 |
| Sorbic Acid | 0.20 |
| Phosphoric Acid | to pH 3.0 |
| Fragrance | 0.20 |
| Water | qs |

The lotions on the hair on each side of the scalp were allowed to remain for a period of 30 minutes, after which they were rinsed away with water. The hair was then shampooed and blown dry. The following evaluations comparing the hair on the right and left side of the scalp were made. The results of this evaluation are reported in Table III.

TABLE III

| | Left Side | Right Side |
|---|---|---|
| HAIR COLORING PROCESS | | |
| Ease of Application | good | excellent |
| Processing Time | 30 min. | 30 min. |
| Skin and Scalp Irritation | none | none |
| Penetration | good | excellent |
| Ease of Rinse-Out | good | good |
| WET EVALUATION OF HAIR | | |
| Feel | fair | good |
| Dryness | dry | fully conditioned |
| Combability | fair | good |
| Manageability | fair | good |
| Snarling | slight | none |
| Porosity | slight | none |
| DRY EVALUATION OF HAIR | | |
| Combability | fair | good |
| Snarling | some | none |
| Coverage of grey | good | excellent |
| Overall coverage | good | excellent |
| Softness | fair | good |
| Body | fair | excellent |
| Manageability | fair | excellent |
| Conditioning | little | very good |
| Luster | fair | excellent |
| HAIR CONDITION AFTER 3 WEEKS | | |
| Tone at Roots | lighter | somewhat darker |
| Blending on Shaft | fair | good |
| Coverage at ends | good | excellent |
| Lifting of color (pigmented hair) | good | excellent |
| Color Retention (overall) | good | excellent |
| Fading (overall) | some | none |
| Skin and Scalp Irritation | none | none |

Comparable results are obtained with the other lactams of this invention, particularly important are methyl didodecyl-[N-(2-pyrrolidonyl)methyl]chloride, methyl dihexadecyl-[N-(2-pyrrolidonyl)methyl]chloride, methyl dioctadecyl-[N-(2-pyrrolidonyl)methyl]chloride, dimethyl hexadecyl-[N-(2-pyrrolidonyl)methyl]chloride, dimethyl tetradecyl-[N-(2-pyrrolidonyl)methyl]chloride, dimethyl octadecyl-[N-(2-pyrrolidonyl)methyl]chloride.

In a similar manner, between about 0.5 wt. % and about 7.5 wt. % of the lactams of this invention can be added to a conventional shampoo tint to improve dye penetration and dye resistance to fading. As described, the lactam is added just prior to use.

Many other substitutions and modifications will become apparent from the foregoing disclosure without departing from the scope of this invention.

What is claimed is:

1. A permanent hair color altering composition containing a permanent hair color altering vehicle and an effective hair penetrating amount of a penetrating agent of a quaternized amino lactam having the formula:

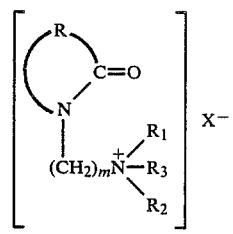

wherein m is an integer having a value of from 1 to 4; R is linear alkylene having from 3 to 8 carbon atoms and is optionally substituted with $C_1$ to $C_4$ alkyl; $R_1$, $R_2$ and $R_3$ are each independently selected from the group of alkyl, alkyleneoxy alkyl, alkylhydroxy, alkoxy, aryl, aralkyl, alkaryl, and alkylene amidoalkyl radicals, said groups each having from 1 to 30 carbon atoms and at least one of $R_1$, $R_2$ and $R_3$ is a radical having from 8 to 30 carbon atoms; and $X^-$ is a chloride, bromide or iodide anion.

2. A composition of claim 1 containing between about 0.5 wt. % and about 7.5 wt. % of said quaternized amino lactam.

3. A hair bleaching composition of claim 1 containing between about 0.01 wt. % and about 12 wt. % of said quaternized amino lactam.

4. The hair bleaching composition of claim 3 containing hydrogen peroxide and an ammonia containing activator.

5. The composition of claim 4 wherein said composition is an aqueous solution.

6. The composition of claim 4 wherein said composition is a cream.

7. A permanent hair coloring composition containing between about 0.01 wt. % and about 12 wt. % of the quaternized amino lactam of claim 1.

8. The hair coloring composition of claim 7 containing an oxidation dye as the hair coloring agent and an oxidizing agent.

9. The composition of claim 8 wherein said composition is an aqueous solution.

10. The composition of claim 8 wherein said composition is a cream.

11. The composition of claim 8 formulated in a shampoo composition.

12. A permanent hair coloring composition comprising an alkaline solution of a phenylene diamine hair dyeing agent at pH of from 9 to 11, a peroxide containing oxidizing dye developer and an effective conditioning amount of the quaternized amino lactam of claim 1.

13. The permanent hair color altering composition of claim 1 wherein said lactam has the formula

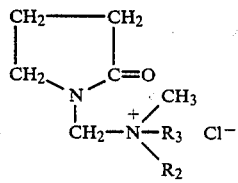

wherein at least one of $R_2$ and $R_3$ is selected from the group consisting of octadecyl, tetradecyl, hexadecyl, hydrogenated tallow and coco and the other of $R_2$ and $R_3$ is methyl or the same as $R_3$.

14. The process of applying to the hair a bleaching composition containing an effective hair conditioning amount of the quaternized amino lactam of claim 1.

15. The process of claim 14 wherein the effective amount of quaternized amino lactam is between about 0.5 and about 7.5 wt. %, based on total composition.

16. The process of claim 14 wherein said quaternized amino lactam is added to said bleaching composition immediately before applying to the hair.

17. The process of applying to the hair a permanent hair coloring composition and an effective hair conditioning amount of the quaternized amino lactam of claim 1.

18. The process of claim 17 wherein the effective amount of quaternized amino lactam is between about 0.5 and about 7.5 wt. %, based on total composition.

19. The process of claim 17 wherein said quaternized amino lactam is added to the hair coloring composition immediately before applying to the hair.

20. The process of claim 19 wherein said permanent hair coloring composition consists essentially of a dye formulation and a developing formulation and wherein said quaternized amino lactam is added to at least one of said formulations prior to their mixture and application to hair.

21. The process of applying to the hair a shampoo tint containing an effective hair conditioning amount of the quaternized amino lactam of claim 1.

22. The process of claim 21 wherein said effective amount of quaternized amino lactam is between about 0.5 and about 7.5 wt. %, based on total composition.

23. The process of claim 14 wherein m of the quaternized amino lactam has a value of 1.

24. The process of claim 17 wherein m of the quaternized amino lactam has a value of 1.

25. The process of applying to the hair a bleaching composition containing an effective hair conditioning amount of the quaternized amino lactam of claim 13.

26. The process of applying to the hair a permanent hair coloring composition and an effective hair conditioning amount of the quaternized amino lactam of claim 13.

27. The process of claim 26 wherein said permanent hair coloring composition consists essentially of a dye formulation and a developing formulation and wherein said quaternized amino lactam is added to at least one of said formulations prior to their mixture and application to hair.

28. The process of applying to the hair a shampoo tint containing an effective hair conditioning amount of the quaternized amino lactam of claim 13.

* * * * *